United States Patent [19]

Gillespie

[11] Patent Number: 4,820,693
[45] Date of Patent: Apr. 11, 1989

[54] METHOD AND COMPOSITION FOR ARRESTING ANGIOGENESIS AND CAPILLARY, CELL OR MEMBRANE LEAKAGE

[75] Inventor: Larrian Gillespie, Brentwood, Calif.
[73] Assignee: Angiogenics, Ltd., San Francisco, Calif.
[21] Appl. No.: 20,859
[22] Filed: Mar. 2, 1987

Related U.S. Application Data

[63] Continuation-in-part of Ser. No. 865,981, May 22, 1986, abandoned, which is a continuation-in-part of Ser. No. 848,288, Apr. 4, 1986, abandoned.
[51] Int. Cl.$^4$ .................. A61K 31/70; A61K 31/725; A61K 31/56
[52] U.S. Cl. ........................................ 514/25; 514/56; 514/169; 514/179
[58] Field of Search .......................... 514/56, 169, 179

[56] References Cited

U.S. PATENT DOCUMENTS

| | | | |
|---|---|---|---|
| 4,510,084 | 4/1985 | Eibl et al. | 530/393 |
| 4,656,161 | 4/1987 | Herr | 514/56 |
| 4,699,900 | 10/1987 | Bayol et al. | 514/54 |
| 4,713,373 | 12/1987 | Bayol et al. | 514/54 |
| 4,738,955 | 4/1988 | Landsberger | 514/56 |

FOREIGN PATENT DOCUMENTS

| | | |
|---|---|---|
| 0114589 | 8/1984 | European Pat. Off. |
| 0140781 | 5/1985 | European Pat. Off. |
| 2201350 | 7/1973 | Fed. Rep. of Germany |

OTHER PUBLICATIONS

"Antibiotic-Induced Interstitial Cystitis: A Model for Cell Membrane Instability", by Gillespie et al., American Urol, Assoc., *Journal of Urology*, 80th Annual Meeting of the AUA in Atlanta, Ga., Apr. 10, 1985.
"Immune-Mediated Angiogenesis Inhibition through SP54 and Prednisone in Antibiotic-Related Interstitial Cystitis", by Gillespie et al., published in Apr., 1986, in the *Journal of Urology*, vol. 135.
"Antibiotic-Related Interstital Cystitis: A Leaky Cell Membrane Disease", by Gillespie et al., presented at 1986 Meeting of American College of Obstetricians and Gynecologists.
Abstract: "Immune-Medicated Angiogenesis Inhibition through SP54 and Prednisone in Antibiotic-Related Interstitial Cystitis", by Gillespie et al., published in Apr. 1986, presented to American Urilogical Assoc. on May 20, 1986.
Abstract: "Antibiotic-Related Interstitial Cystitis: A Leaky Cell Membrane Disease" by Gillespie et al., presented at a 1986 Meeting of the American College of Obstetricians and Gynecologists.
Article: (Studies on the Modifying Effect of Dimethyl Sulfoxide and Other Chemicals on Experimental Skin Tumor Induction) Stenback et al., Annals New York Academy of Sciences, vol. 243; 1975, pp. 209-227.
Abstract: (Antibiotic-Induced Interstitial Cystitis: an Auto-Immune Phenomenon), Gillespie et al., Abstract No. 108, published Jul. 16, 1984.
Abstract: (Antibiotic-Induced Interstitial Cystitis: A Model for Cell Membrane Instability), Gillespie et al., American Urol. Assoc., Journal of Urology, 80th Annual Meeting of the AUA in Atlanta, Ga., Apr. 10, 1985.
"Pharmacologic and Biochemical Considerations of Dimethyl Sulfoxide", by Wood et al., *Annals New York Academy of Sciences;* vol. 243; 1975, pp. 7-19.
Article: (A New Class of Steroids Inhibits Angiogenesis in the Presence of Heparin or a Heparin Fragment), Crum et al., *Science;* 12/20/85, pp. 1375-1378.
Article: (The Use of Dimethyl Sulfoxide in the Treatment of Intractable Urinary Frequency), Okamura et al., *Acta Urol.*, vol. 31(4); 1985, pp. 627-632.
Article: (Pharmacologic and Biochemical Considerations of Dimethyl Sulfoxide), Wood et al., *Annals New York Academy of Sciences*, vol. 243; 1975, pp. 7-19.
"Prospective Study of Intravesical Dimethyl Sulfoxide in Treatment of Suspected Early Interstitial Cystitis", by Fowler, *Urology*, vol. 18(1); Jul. 1981, pp. 21-26.
"Anti-Angiogenesis by Steroids without Glucocorticoid or Mineralocorticoid Activity in the Presence of Heparin", by Crum et al., *Journal of Cell Biology;* Oct. 1984, Abstract No. 581, p. 158a.
"Successful Treatment of Interstitial Cystitis with Sodium Pentosanpolysulfate", by Parsons et al., *Journal of Urology;* 1983, pp. 51-53.
"The Effect of Pentosan Polysulfate (SP54) on the Fibrinolytic System of Man", by Marsh et al., *IX International Congress on Thrombosis and Hemostasis*—Stockholm, 1983, Abstract 0246.
Article: (Angiogenesis Inhibition and Tumor Regression Caused by Heparin or a Heparin Fragment in the Presence of Cortisone), Folkman et al., *Science;* 8/83, pp. 719-725.
Article: (Vascularization Induced in the Cheek Pouch of the Syrian Hamster . . . ), Shubik et al., *Journal of the National Cancer Institute*, vol. 57; 10/76, pp. 769-774.
Article: (Toward a New Understanding of Vascular Proliferative Disease in Children), Folkman, Pediatrics, vol. 74; 11/5/84, pp. 850-856.

*Primary Examiner*—John W. Rollins
*Attorney, Agent, or Firm*—Sandler & Greenblum

[57] ABSTRACT

A composition and method for arresting angiogenesis, and cell, capillary or membrane leakage comprising a pharmaceutically effective amount of angiostatic steroid and pentosan polysulfate, or a salt thereof, having the formula:

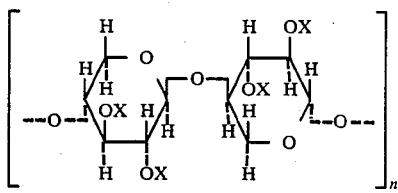

wherein X is at least one member selected from the group consisting of H and —SO$_3$Y, and Y is at least one member selected from the group consisting of H and a pharmaceutically acceptable cation.

53 Claims, No Drawings

METHOD AND COMPOSITION FOR ARRESTING ANGIOGENESIS AND CAPILLARY, CELL OR MEMBRANE LEAKAGE

CONTINUING DATA

The instant application is a Continuation-in-Part of U.S. patent application Ser. No. 865,981, filed May 22, 1986, now abandoned, which is a Continuation-in-Part of U.S. patent application Ser. No. 848,288, filed Apr. 4, 1986, now abandoned. The disclosures of both Applications are incorporated in their entireties by reference thereto.

BACKGROUND OF THE INVENTION

1. Field of the Invention

The present invention relates to novel compositions useful for arresting angiogenesis and membrane, cell or capillary leakage when used in effective amounts, and to methods of administering such compounds for purposes of arresting membrane leakage or capillary leakage, such as in abnormal angiogenesis, e.g., abnormal capillary growth.

2. Description of Background and Relevant Materials

Steroids generally have constituted a standard treatment when administered topically, percutaneously and intravenously by virtue of their anti-inflammatory effects.

Heparin and heparin fragments, when used alone have been reported to enhance tumor angiogenesis ("Angiogenesis Inhibition and Tumor Regression Caused by Heparin or a Heparin Fragment in the Presence of Cortisone", by Folkman et al. Science (1983) 221:719-725. The same article reports that angiogenesis can be inhibited by the combination of heparin and cortisone based upon animal tests. No human tests were conducted.

European Pat. No. 0 114 589, published Aug. 1, 1984, in the name of FOLKMAN et al., as well as the above article disclose a technique for the inhibition of angiogenesis in mammals by treatment with heparin and specific heparin fragments, in combination with a member selected from cortisone, hydrocortisone or the 11-alpha isomer of hydrocortisone so as to inhibit angiogenesis with subsequent regression of large tumor masses and alleged prevention of tumor metastasis in mammals.

In these materials engiogenesis is defined as the growth of new capillary blood vessels which is important in normal tissue growth such as the development of the embryo, formation of the corpus luteum and wound healing. It is also stated to be a component in pathologic processes such as chronic inflammation, certain immune responses and neoplasia. Angiogenesis is stated to be a property of most solid tumors and is necessary for their continued growth.

The patent application reports that heparin alone enhances the intensity of angiogenesis induced by tumors in vivo. Reference is made to work by SHUBIK et al. (J. Natl. Cancer Inst., Vol. 57, 769-774, [1976]) in which 6 alphamethyl-prednisolone partially suppressed tumor angiogenesis in hamster cheek pouch under certain conditions. Other publications have reported continued growth of tumors even in the presence of large doses of cortisone.

The application goes on to state that heparin fragments which are hexasaccharide or larger together with cortisone or hydrocortisone or the 11-alpha isomer of hydrocortisone will inhibit angiogenesis in mammals.

The effect on angiogenesis is more definitively discussed in an article entitled: Toward a New Understanding of Vascular Proliferative Disease in Children, Pediatrics, Vol. 74, No. 5, November 1984.

The use of the purified form of heparin and heparin fragment in combination with certain steroid is also suggested by Crum et al., J. Cell Biology, October 1984, Abstract No. 581, page 158a.

The patent application is silent as to a key aspect of the mechanism behind angiogenesis, namely capillary exchange or leakage which Applicant alone has recognized to be the fundamental mechanism underlying angiogenesis.

In another approach, the use of sodium pentosan polysulfate $SP_{54}$, as an alternative to heparin, in the treatment of interstitial cystitis is disclosed (Successful Treatment of Interstitial Cystitis with Sodium Pentosanpolysulfate, by C. Lowell Parsons et al., Journal of Urology. pp. 51-53, 1983). The authors indicate that $SP_{54}$ is safe in humans, but mistakenly conclude that the method of action of the compound was through excretion in urine, and the relationship between the disease and its treatment to angiogenesis is not appreciated. This has now been found to be erronous because the fragment is destroyed in the kidney. The lower anticoagulant activity of the compound in comparison to heparin is also disclosed, see also Marsh, N. Gaffney, P. J.: The Effect of Pentosan Polysulfate ($SP_{54}$) on the Fibrinolytic System of Man, IX Int. Congress on Thrombosis and Haemostasis, Stockholm, 1983.

The principles underlying the efficacy of particular steroids in arresting angiogenesis, in the presence of heparin fragments has been studied and reported by Crum et al., A New Class of Steroids Inhibits Angiogenesis in the presence of Heparin or a Heparin Fragment, Science, Vol. 230, 1375-1378, (1985). The article identifies the minimum essential structure of a steroid necessary to exhibit angiostatic properties. It is recognized that this steroid function is independent of glucocorticoid and mineralcorticoid activity.

Dimethyl sulfoxide, which also is used in the composition of the invention, has previously been known in the treatment of patients with intractible urinary frequency due to chronic prostatitis, chronic cystitis, tuberculous contracted bladder and interstitial cystitis (Okamura et al., Acta Urol. Japan, 31(4), 1985, 627-632; Fowler, J. E., Urol., 18(1), 1981, 21-26). Dimethyl sulfoxide (DMSO) which has been in use for many years has a number of interesting properties. Perhaps one of the most interesting and significant properties of DMSO is its ability to move other drugs through membranes. When mixed with DMSO many drugs appear to be potentiated in their physiologic effect. Thus, smaller drug dosages are required and less toxicity is demonstrated, WOOD et al., ANN.N.Y. Acad. Sci., 1975, vol. 243 (7-19). For this reason, investigations have been previously conducted on the use of dimethyl sulfoxide to increase the ability of chemicals to penetrate through the skin, a process which was reported to possibly contribute to tumor formation (Stenback, F. et al., A. N. Y. ACAD. Sci., 1975, vol. 243 (209-227). The same article studies the effects of adding other anti-inflammatory agents such as cortisone on tumorigenesis.

The inventor has previously reported the efficacy of dimethyl sulfoxide in the treatment of a specific type of interstitial cystitis—antibiotically induced—in combination with steroid and sodium bicarbonate buffer in a published Abstract, ANTIBIOTIC-INDUCED INTERSTITIAL CYSTITIS: AN AUTO-IMMUNE PHENOMENON, Abstract #108, published July 16, 1984, Abstract presented to American Urological Association, Western Section Meeting, Reno, Nevada; Antibiotic-Induced Interstitial Cystitis: A Model for Cell Membrane Instability, L. Gillespie, et al., Amer. Urological Association, Journal of Urology, 80th Annual Meeting of the AUA in Atlanta, Ga., Apr. 10, 1985. These reports, however, were silent as to the use of pentosan polysulfate, and angiogenesis was never specifically mentioned.

SUMMARY OF THE INVENTION

It is, therefore, an object of the invention to provide a novel therapeutic composition for arresting angiogenesis, and cell, capillary or membrane leakage comprising a pharmaceutically active amount of angiostatic steroid and a pentosan polysulfate, or a salt thereof, having the formula:

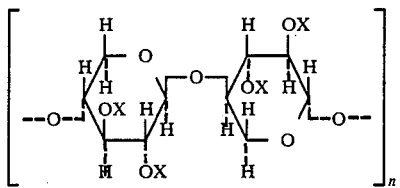

wherein X is at least one member selected from the group consisting of H and —SO$_3$Y, and Y is at least one member selected from the group consisting of H and a pharmaceutically acceptable cation.

It is further an object of the invention to provide a method of arresting angiogenesis, and cell or membrane leakage by administration of the compound.

Preferably, the pentosan polysulfate has a sulfur content of approximately 14-20% by weight, and a —SO$_3$Y unit content of approximately 1.5-2.0 —SO$_3$Y units per monosaccharide unit. Most preferably, the pentosan polysulfate is substantially fully sulfated: i.e., substantially all of the hydroxy groups have been converted to —SO$_3$Y units.

The molecular weight of the pentosan polysulfate of the invention is preferably approximately 1,600-6,000, or, more preferably, approximately 2,000. The pentosan polysulfate preferably also has substantially no anticoagulant properties. In one preferred commercially available composition, the pentosan sulfate is the sodium salt of the substantially fully sulfated pentosan polysulfate.

The angiostatic steroid is selected from the group of: cortisone, hydrocortisone, 11 alpha epihydrocortisol, tetrahydro S, and 17 alpha hydroxy progesterone.

The composition may further include a buffering agent in an amount sufficient to maintain a pH of at least about 8 to prevent deactivation of the antigiostatic steroid when exposed to an acidic environment in the body.

The composition may further include a pharmaceutically effective amount of dimethyl sulfoxide.

A four component composition may include pharmaceutically effective amounts of the pentosan polysulphate, angiostatic steroid, and DMSO, together with sufficient amounts of buffer.

When the composition is to be orally administered one preferred angiostatic steroid is delta cortisone, in combination with the pentosan polysulfate, in pharmaceutically effective amounts.

The composition of the invention may be in non-aqueous powdered or pill form in which case angiostatic steroids having low water solubilities are administered in combination with the pentosan polysulfate. The most preferred water insoluble angiostatic steroid is delta cortisone.

The inventive composition may be formulated in aqueous form in which case the angiostatic steroid is selected from the group consisting of: cortisone, hydrocortisone, 11 alpha epihydrocortisol, tetrahydro S, and 17 alpha hydroxy progesterone. The aqueous composition further includes DMSO to improve transport of the compound, and may further include buffer, as noted above.

The composition of the invention has proven useful in treating bladder cancer and other diseases.

DESCRIPTION OF PREFERRED EMBODIMENTS

It has been discovered that combinations of certain steroids and pentosan polysulfate, and salts thereof, unexpectedly, when administered in pharmaceutically effective amounts succeed in arresting angiogenesis, cell membrane leakage, and capillary leakage or exchange.

Cell membrane leakage has now, in tests conducted by Applicant, been discovered to be the cause of a number of different diseases whose basis was not previously understood. Thus, antibiotic-induced interstitial cystitis is a specific disease entity which presents with pelvic pain before and after voiding, frequency and nocturia in the absence of infection with an alkaline urine. Arthritic symptoms, spastic colon and low grade fevers were seen in 34% of patients suspected of having the disease. Three hundred patients were cystoscoped under anesthesia and demonstrated petechial hemorrhaging, glomerulation or linear striation after decompression of the bladder. Bladder biopsies demonstrated loss of the surface glycosaminoglycans layer (GAG) with resultant loss of cellular integrity of the urothelial cells.

In a disease such as this, whereas prior treatments had been ineffective, treatment aimed at arresting angiogenesis and/or membrane and capillary leakage have now been found to provide cure in many cases.

The composition of the invention has been found to provide surprisingly good results in providing relief and cure, without disturbing side effects which are anticipated when purified and highly toxic forms of heparin and steroids are used. For example, research by the inventor has now shown that the leaky cell theory also explains immunemediated angiogenesis, including immunological interstitial cystitis, chronic cystitis, trigonitis, urethritis, arthritis, diabetes, certain types of tumor growth, including transitional cell carcinoma of the bladder, angiofibromas, angiosarcoma, bladder cancer, renal cell carcinoma, cervical cancer, hemangiomas and other vascular lesions, inflammatory angiogenesis including DES (diethylstilbesterol) cervicitis, psoriasis, vaginosis, inflammatory interstitial cystitis and other inflammatory conditions.

In contradistinction to the disclosure of European Patent Application 0 114 589, the instant invention is specifically directed to the use of pentosan polysulfate, or salts thereof, which can be characterized as a linear anionic polyelectrolyte of the sulphated polyanion type. While similar compounds covalently bound with protein naturally exist in blood and tissue where they enhance various systems and control enzyme reactions by virtue of density and distribution of the electronegative charge, such heparins are heterogeneous with respect not only to their molecular weight but also to the distribution of active groups. It is a specific aim of the instant convention, therefore, to specifically utilize pentosan polysulfate, or salts thereof, which are chemically well defined with constant pharmacological potency.

The base units of the pentosan polysulfate are pentoses, with a polymer chain being made of 1-4 linked beta-D-xylopyranose residues as is shown by the following structural fragment, which depicts hydroxy groups completely converted to the sulfate radicals and substituted with sodium:

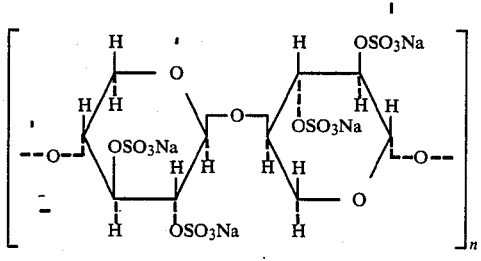

Because beta-glucosides do not show much natural tendency to form helices and the large number of negatively charged, mutually repelling S4 groups also tend to prevent coiling, this results in the polymer adopting a fairly rigid and linear configuration.

The preferred pentosan polysulfate has a sulfur content of approximately 14-20 percent by weight, and a sulfate radical content of approximately 1.5-2.0 sulfate radicals per monosaccharide unit. Most preferably, the pentosan polysulfate is substantially fully sulfated: i.e., substantially all of the hydroxy units have been converted to sulfate radicals.

As used herein, the term "pentosan polysulfate" also includes salts thereof: i.e., the H of the sulfate radical being replaced with a pharmaceutically acceptable cation. Also as used herein, the term "sulfate radical" refers both to $-OSO_3H$ groups, and to such groups where the H has been replaced by a pharmaceutically acceptable cation.

Pentosan polysulfate salts selected from the group of: potassium, sodium, magnesium, ammonium salts, as well as other salts, may be used.

The molecular weight of the pentosan polysulfate according to the invention is preferably between approximately 1,600-6,000. A molecular weight composition of 2,000 is particularly preferred. One commercially available form of the sodium polyanion salt is SP$_{54}$, sold by BENE ARZNEIMITTEL GMBH, 8,000 Munich 71, Federal Republic of Germany.

U.S. Pat. No. 4,699,900, issued Oct. 13, 1987, and U.S. Pat. No. 4,713,373, issued Dec. 15, 1987, both in the name of BAYOL et al., disclose that the present state of the art for analytically defining SP$_{54}$ is inexact, and that several researchers have given different results for the same product.

BAYOL et al. '900 discloses that SP$_{54}$ has been determined to have the random structural formula:

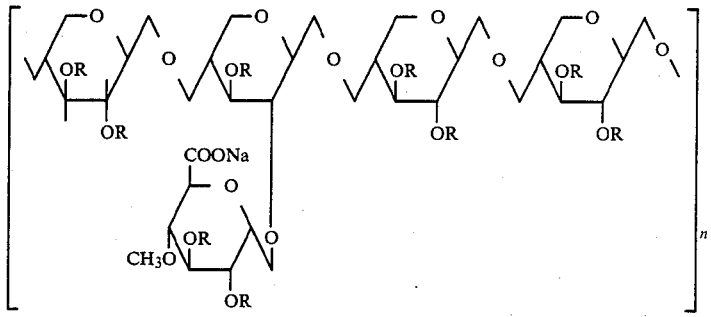

wherein R is $-SO_3Na$ or hydrogen in such amounts that the polysaccharide has 1.81 $-SO_3Na$ units per monosaccharide unit.

BAYOL et al. '900 further indicates that SP$_{54}$ has been determined to be defined by the following characteristics:
 $\overline{Ma}$ (apparent average molecular weights): 6000;
 $\overline{Mn}$ (number average molecular weights): 5400;
 $\overline{Mw}$ (weight average molecular weights): 7000;
 Dispersion: $D = \overline{Mw}/\overline{Mn} = 1.29$;
 Percent uronic acids: 5.8;
 Percent pentoses: 35.5.

BAYOL et al. '373 also discloses SP$_{54}$ as having been determined to have the same statistical formula, with 1.5-2, and, more precisely, close to 1.8-SO$_3$Na groups per monosaccharide unit, and as being characterized by a mixture of polymers of polar masses which comprise 1,000-40,000 Daltons, and have quasigaussian distribution.

Other characteristics of SP$_{54}$ are indicated in BAYOL et al. '373 to include the following:
 $\overline{Mn}$ (Average number molecular mass): 5300-5500;
 $\overline{Mw}$ (Average weight molecular mass): 7400-7600;
 $D = \overline{Mw}/\overline{Mn}$ (Polydispersity Index—measuring the width of the molecular distribution): 1.4-1.5
 $\overline{Ma}$ (Apparent average mass; corresponding to the majority isomolecular population in concentration, i.e., the top of the peak on the chromatogram): 6500-7200 D;
 Average determination by weight of sulfur: 15-20%;
 Percentage by weight of pentoses, expressed as xylose equivalent: 30-40%;
 Percentage by weight uronic acids, expressed as glucuronic acid: 4-6%.

The indicated measurement of uronic acids is indicated to correspond to a proportion of 1 glucuronic unit per 8-10 xylose units. Further, the uronic acids are indicated principally to be 4 MeO-glucuronic acid.

When used alone, the sulphated polyanion exhibits significant thrombolytic, fibrinolytic and lipolytic action. Yet, unlike heparin, it is virtually free of any anticoagulant effect.

When used in combination with angiostatic steroids generally, the combination has proven unexpectedly useful in overcoming the effects of membrane leakage which have been the root cause of the diseases recited above.

The pentosan polysulfate and steroid may be mixed together prior to administration or may be administered separately. The administration may be oral or parenteral including inter alial topical application, intravenous, intra-arterial or subcutaneous injection, and including absorption as well as injection and introduction into bodily apertures or orifices. The dosages administered are a function of the manner of administration.

Depending upon the type of administration, the following concentrations are preferred: topical application-DMSO 50 cc., 100 mg. angiostatic steroid, e.g. hydrocortisone, 50 meq. NaHCO$_3$ and up to 200 mg. pentosan polysulphate, or the salt thereof; intravenous-pentosan polysulphate up to 400 mg., 700 mg. hydrocortisone, every 8 hours; intra-arterial-continual infusion of 400–800 mg. pentosan polysulphate, 200 mg. hydrocortisone, every 8 hours, subcutaneous injection-100–400 mg. pentosan polysulphate, 50 mg. hydrocortisone every 8 hours.

By way of example, when applied directly to the bladder, dosages on the order of 50 cc. DMSO, 100 mg. hydrocortisone, 100 mg. pentosan polysulphate, and 50 meq. NaHCO$_3$ are preferred.

Although the above ranges have been provided as general guides, it is to be understood that dosage will vary as a function of body weight, tumor type and size, manner of administration, etc.

When administered directly to cavities or organs wherein acid conditions may adversely effect the steroid, it is necessary that a buffering agent be incorporated in sufficient amounts so as to maintain a pH of about 8 or above so as to prevent deactivation of the steroid. Amounts on the order of 50 milliequivalents are preferred.

A buffering agent used according to the invention is most preferably sodium bicarbonate, although other buffering agents such as magnesium, potassium, or calcium bicarbonate may also be used.

In other than oral, intravenous, intra-arterial, or intra-alial administration, the effectiveness of the treatment is vastly improved if dimethyl sulfoxide (DMSO) is added to the mixture in amounts of between 25–50 cc of about 50% aqueous DMSO. DMSO is a known potentiator which functions as a transport vehicle which allows the mixture of the invention to immediately penetrate and flow into the individual cells.

While it was originally suspected that DMSO might work to have exactly the opposite of the desired effect because of the possibility that it might spread the agent responsible for abnormal cell growth beyond the area of abnormality into healthy tissue, this has not been found to occur.

Thus, the use of a composition comprising steroid, pentosan polysulfate, DMSO, and a buffering agent constitute a novel composition exhibiting unexpected and improved results.

According to the invention the steroids used are angiostatic steroids. Anti-angiogenic or angiostatic activity is associated with the pregnane structure, and governed mainly by structural components on the D ring of the steroid. The 4,5 double bond in the A ring and the 11-hydroxyl on the C ring are not essential for angiostatic activity. Absence of the 17-hydroxyl and of carbons 20 and 21 on the D ring leads to successive reduction of angiostatic activity.

Deltacortisone can only be used orally since it is not water soluble to a sufficiently substantial extent. For other types of administration, angiostatic compounds used according to the invention must be of low water solubility. Deltacortisone has a half life of approximately 8 to 10 hours such that it is far more effective when administered orally than steroids having shorter half lives.

Steroids generally have a low predictability, such that even analogues do not function predictably. Deltacortisone has not previously been disclosed for use in combination with heparin fragments generally, or pentosan polysulfate. A number of other steroids were tested, with heparin and heparin fragments, but were found ineffective in overcoming angiogenesis discussed above. These unsuccessful compounds included dexamethasone, corticosterone, desoxycorticosterone, progesterone, estrone, testosterone, and cholesterol, pregnenolone, and cortexolone.

When administering topically, the steroid of choice is of the water soluble angiostatic group: cortisone, hydrocortisone, 11 alpha epihydrocortisol, tetrahydro S, 17 alpha hydroxy progesterone.

According to one embodiment of the invention, the mixture of the present invention may be administered from a container such as a bottle, having a first compartment and a second compartment separated by a breakable barrier such as a diaphragm. The first compartment contains a powdered angiostatic steroid of the invention and powdered pentosan polysulphate, while the second compartment contains a liquid mixture of buffering agent.

When the mixture of the invention is to be applied topically, the DMSO is added to the second compartment containing the buffering agent. When the barrier is broken, such as by twisting and pushing the diaphragm down in the bottle, the contents of the first and second compartments are mixed and the steroid becomes activated by reason of the alkaline pH provided by the buffering agent. The actual way in which the components are divided is not critical except that the steroid and pentosan polysulphate must be separated from the buffer in the liquid state. The solution is then drawn up into a syringe in communication with the container for intravenous injection.

The container may be provided with an applicator means in communication with one of the compartments for topical application to the area of interest.

Although DMSO is known as a transport agent, the mechanism through which it functions to penetrate membranes is not well understood. Thus, for example, certain compounds, e.g., morphine and xylocane, when mixed with DMSO, serve to deactivate the DMS and negate its activity. This is believed to occur because these other compounds prevent calcium ion influx across the cell membrane, an important mechanism by which DMSO causes cellular penetration. Because pentosan polysulfate and steroids are stabilizers, i.e., these compounds are considered to prevent cell leakage, the DMSO might have been thought to be deactivated. It has now been surprisingly found instead that the DMSO operates for its intended function as a transport agent without affecting this mechanism, as will be seen from the Examples which follow.

EXAMPLES

Example 1

Sixty-four interstitial cystitis subjects were studied by immunofluorescence. Antigenic staining for IgM with or without C3 was found in the capillaries of the interstitium in the sixty four patients indicating immune angiogenesis. The patients were treated by target therapy with a catheter using 100 mg SP$_{54}$, 100 mg hydrocortisone, 50 milliequivalent sodium bicarbonate, 50 cc 50% DMSO. Average treatment was once a week for two months. When treated with DMSO, Solucortef and NaHCO3 only 2 out of 64 patients with antigenic staining for IgM in the capillaries of the bladder were stabilized. Cure was measured by the absence of antigenic staining for IgM on repeat biopsy and relief of all symptoms including frequency, burning, pelvic pressure, nocturia, with return of urinary pH to 5 (acidic). Negative staining corresponded to relief of symptoms, and an increase in functional capacity. When, in addition, SP$_{54}$ was added to the treatment, another 46 out of the same 64 patients (approximately 72%) showed cure, indicating that the inventive composition arrested angiogenesis.

Example 2

Eighty-one patients exhibiting IgM vasculitis on bladder biopsies were orally administered the composition of the invention in liquid and/or pill at dosages of 200-400 mg./day SP$_{54}$ and 10 mg. Prednisone twice a day every other day, for up to 11 months. About 76 responded extremely well to oral therapy, showing complete relief of symptoms. Ten patients were re-biopsied and there was no IgM staining present in those who responded. In those who did not respond IgM staining was identical to the original staining. Therapy could be reduced or stopped altogether in 18 patients with no recurrence after 5 months.

Example 3

Three patients with grade 1-3 transitional cell carcinoma of the bladder with one case of carcinoma in situ were treated with intravesical 50 cc DMSO, 100 mg. SP$_{54}$, 100 mg. hydrocortisone, and 50 meq. sodium bicarbonate on a weekly basis for six weeks. Repeat cystoscopy showed complete remission of the tumors and re-biopsy demonstrated no evidence of carcinoma in situ nor of transitional cell carcinoma.

Example 4

100 mice injected with live transitional cell carcinoma subcutaneously, and were grown to a maximum size of 2 cm. prior to therapy. The mice were given SP$_{54}$ and hydrocortisone orally and by injection. The composition was orally administered with SP$_{54}$ at 0.06 mg./ml. and hydrocortisone at 0.5 mg./ml. in drinking water. In others the composition was injected with 0.66 mg./ml. SP$_{54}$ and hydrocortisone at 3 mg./ml. twice daily, 0.55 cc. Both types of administration resulted in tumor regression. When SP$_{54}$ was eliminated from treatment the mice developed regression of tumor but were found to have lung metastasis which were not found in those mice treated with SP$_{54}$ and angiostatic steroid.

Example 5

A patient exhibiting DES cervicitis was followed for 18 years with pap smear, colposcopy and cervical biopsies, every 3 months for 18 years. The solution of the invention was applied to the vagina and cervix once in a concentration of 100 mg. SP$_{54}$, 100 mg. hydrocortisone, 50 meq. sodium bicarbonate, 50 cc., 50% DMSO, whereupon the patient was re-papped and re-colposcoped at 3 weeks and 3 months. Lesions were found to be healing and within 3 months all studies came back to normal. One year later repeat colposcopies and pap smears remained normal.

Example 6

A 55 year old male was found to have biopsy-proven angiosarcoma of the chest wall; the tumor doubling rate was 24 hours. The patient was started on 60 mg. Prednisone daily and 800 mg. SP$_{54}$ whereupon the tumor stopped doubling.

Although the invention has been described with reference to particular means, materials and embodiments, it is to be understood that the invention is not limited to the particulars disclosed and extends to all equivalents within the scope of the claims.

I claim:

1. A composition for arresting angiogenesis, and cell, capillary or membrane leakage comprising a pharmaceutically effect amount of angiostatic steroid and pentosan polysulfate, having the formula:

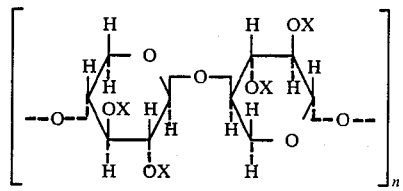

wherein X is at least one member selected from the group consisting of H and —SO$_3$Y, and Y is at least one member selected from the group consisting of H and a pharmaceutically acceptable cation.

2. The composition as defined by claim 1 wherein said pentosan polysulfate has a sulfur content of approximately 14-20% by weight, and a —SO$_3$Y group content of approximately 1.5-2.0—S$_3$Y groups per monosaccharide unit.

3. The composition as defined by claim 2 wherein said pentosan polysulfate has a molecular weight of 1,600-6,000.

4. The composition as defined by claim 3 wherein said pentosan polysulfate has as molecular weight of 2,000 and has substantially no anticoagulant properties.

5. The composition as defined by claim 4 wherein Y is sodium.

6. The composition as defined by claim 1 wherein said angiostatic steroid is selected from the group of: cortisone, hydrocortisone, 11 alpha epihydrocortisol, tetrahydro S, and 17 alpha hydroxy progesterone.

7. The composition as defined by claim 6 further comprising a buffering agent in an amount sufficient to maintain a pH of at least about 8 to prevent deactivation of said antigiostatic steroid when exposed to an acidic environment in the body.

8. The composition as defined by claim 6 further comprising a pharmaceutically effective amount of dimethyl sulfoxide.

9. The composition as defined by claim 6 further comprising a pharmaceutically effective amount of dimethyl sulfoxide, and a buffering agent in an amount sufficient to maintain a pH of at least about 8 to prevent deactivation of said angiostatic steroid when exposed to an acidic environment in the body.

10. The composition as defined by claim 2 wherein said pentosan polysulfate comprises at least one uronic acid unit.

11. The composition as defined in claim 1 wherein said angiostatic steroid is delta cortisone.

12. The composition as defined by claim 1 wherein said pentosan polysulfate comprises at least one uronic acid unit.

13. A non-aqueous composition for oral administration comprising a pharmaceutically active amount of angiostatic steroid and pentosan polysulfate, or a salt thereof, having the formula:

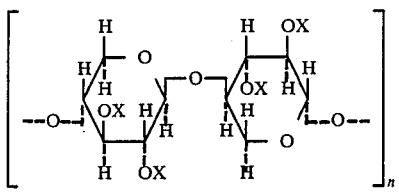

wherein X is at least one member selected from the group consisting of H and —SO₃Y, and Y is at least one member selected from the group consisting of H and a pharmaceutically acceptable cation.

14. The composition as defined by claim 13 wherein said pentosan polysulfate has a sulfur content of approximately 14-20% by weight, and —SO₃Y group content of approximately 1.5-2.0 —SO₃Y groups per monosaccharide unit.

15. The composition as defined by claim 14 wherein said pentosan polysulfate has a molecular weight of 1,600-6,000.

16. The composition as defined by claim 15 wherein said pentosan polysulfate has a molecular weight of 2,000 and has substantially no anticoagulant properties.

17. The composition as defined by claim 16 wherein Y is sodium.

18. The composition as defined by claim 13 wherein said angiostatic steroid is delta cortisone.

19. The composition as defined by claim 13 wherein said pentosan polysulfate comprises at least one uronic acid unit.

20. The composition as defined by claim 14 wherein said pentosan polysulfate comprises at least one uronic acid unit.

21. An aqueous composition for arresting angiogenesis and cell, capillary or membrane leakage comprising a pharmaceutically active amount of angiostatic steroid and pentosan polysulfate, or a salt thereof, having the formula:

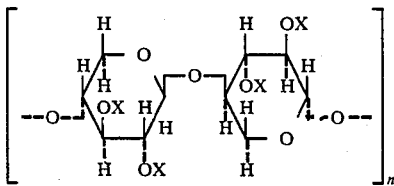

wherein X is at least one member selected from the group consisting of H and —SO₃Y, and Y is at least one member selected from the group consisting of H and a pharmaceutically acceptable cation.

22. The composition as defined by claim 21 wherein said pentosan polysulfate has a sulfur content of approximately 14-20% by weight, and a —SO₃Y group content of approximately 1.5-2.0 —SO₃Y groups per monosaccharide unit.

23. The composition as defined by claim 22 wherein said pentosan polysulfate has a molecular weight of 1,600-6,000.

24. The composition as defined by claim 23 wherein said pentosan polysulfate has as molecular weight of 2,000 and has substantially no anticoagulant properties.

25. The composition as defined by claim 24 wherein Y is sodium.

26. The composition as defined by claim 21 wherein said angiostatic steroid is selected from the group consisting of: cortisone, hydrocortisone, 11 alpha epihydrocortisol, tetrahydro S, and 17 alpha hydroxy progesterone.

27. The composition as defined by claim 21 further comprising a buffering agent in an amount sufficient to maintain a pH of at least about 8 to prevent deactivation of said angiostatic steroid when exposed to an acidic environment in the body.

28. The composition as defined by claim 21 further comprising a pharmaceutically effective amount of dimethyl sulfoxide.

29. The composition as defined by claim 21 further comprising a pharmaceutically effective amount of dimethyl sulfoxide, and a buffering agent in an amount sufficient to maintain a pH of at least about 8 to prevent deactivation of said delta cortisone when exposed to an acidic environment in the body.

30. The composition as defined by claim 21 wherein said pentosan polysulfate comprises at least one uronic acid unit.

31. The composition as defined by claim 22 wherein said pentosan polysulfate comprises at least one uronic acid unit.

32. A method of arresting angiogenesis, and cell, capillary or membrane leakage comprising administering a pharmaceutically effective amount of a composition comprising:
a pharmaceutically active amount of angiostatic steroid and pentosan polysulfate, or salts thereof, having the formula:

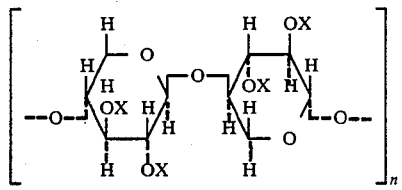

wherein X is at least one member selected from the group consisting of H and —SO₃Y, and Y is at least one member selected from the group consisting of H and a pharmaceutically acceptable cation.

33. The method as defined by claim 32 wherein said pentosan polysulfate has a sulfur content of approximately 14-20% by weight, and a —SO₃Y group content of approximately 1.5-2.0 —SO₃Y groups per monosaccharide unit.

34. The method as defined by claim 33 wherein said pentosan polysulfate has a molecular weight of 1,600–6,000.

35. The method as defined by claim 34 wherein said pentosan polysulfate has a molecular weight of 2000 and has substantially no anticoagulant properties.

36. The method as defined by claim 35 wherein Y is sodium.

37. The method as defined by claim 32 wherein said angiostatic steroid is selected from the group consisting of: cortisone, hydrocortisone, 11 alpha epihydrocortisol, tetrahydro S, and 17 alpha hydroxy progesterone.

38. The method as defined by claim 37, said composition further comprising a buffering agent in an amount sufficient to maintain a pH of at least about 8 to prevent deactivation of said angiostatic steroid when exposed to an acidic environment in the body.

39. The method as defined by claim 37 further comprising a pharmaceutically effective amount of dimethyl sulfoxide.

40. The method as defined by claim 37 further comprising a pharmaceutically effective amount of dimethyl sulfoxide, and a buffering agent in an amount sufficient to maintain a pH of at least about 8 to prevent deactivation of said angiostatic steroid when exposed to an acidic environment in the body.

41. The method as defined by claim 32 wherein said pentosan polysulfate comprises at least one uronic acid unit.

42. The method as defined by claim 33 wherein said pentosan polysulfate comprises at least one uronic acid unit.

43. A method of treating bladder cancer comprising administering a composition comprising:

a pharmaceutically active amount of angiostatic steroid and pentosan polysulfate, or a salt thereof, having the formula:

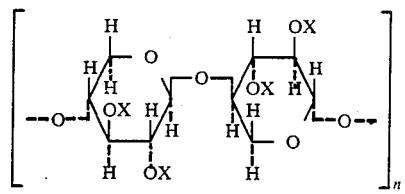

wherein X is at least one member selected from the group consisting of H and —SO$_3$Y, and Y is at least one member selected from the group consisting of H and a pharmaceutically acceptable cation.

44. The method as defined by claim 43 wherein said pentosan polysulfate has a sulfur content of approximately 14–20% by weight, and a —SO$_3$Y group content of approximately 1.5–2.0 —SO$_3$Y groups per monosaccharide unit.

45. The method as defined by claim 44 wherein said pentosan polysulfate has a molecular weight of 1,600–6,000.

46. The method as defined by claim 45 wherein said pentosan polysulfate has as molecular weight of 2,000 and has substantially no anticoagulant properties.

47. The method as defined by claim 46 wherein Y is sodium.

48. The method as defined by claim 43 wherein said steroid is selected from the grpoup consisting of: cortisone, hydrocortisone, 11 alpha epihydrocortisol, tetrahydro S, and 17 alpha hydroxy progesterone.

49. The method as defined by claim 43 further comprising a buffering agent in an amount sufficient to maintain a pH of at least about 8 to prevent deactivation of said angiostatic steroid when exposed to an acidic environment in the body.

50. The method as defined by claim 43 further comprising a pharmaceutically effective amount of dimethyl sulfoxide.

51. The method as defined by claim 43 further comprising a pharmaceutically effective amount of dimethyl sulfoxide, and a buffering agent in an amount sufficient to maintain a pH of at least about 8 to prevent deactivation of said angiostatic steroid when exposed to an acidic environment in the body.

52. The method as defined by claim 43 wherein said pentosan polysulfate comprises at least one uronic acid unit.

53. The method as defined by claim 44 wherein said pentosan polysulfate comprises at least one uronic acid unit.

* * * * *

UNITED STATES PATENT AND TRADEMARK OFFICE
CERTIFICATE OF CORRECTION

PATENT NO. : 4,820,693

DATED : April 11, 1989

INVENTOR(S) : L. GILLESPIE

It is certified that error appears in the above-identified patent and that said Letters Patent is hereby corrected as shown below:

Title page, first column, under the heading "OTHER PUBLICATIONS", fourth paragraph, first line, change "Medicated" to ---Mediated---.

Title page, first column, under the heading "OTHER PUBLICATIONS", fourth paragraph, fourth line, change "Urilogical" to ---Urological---.

Column 1, line 47, change "engiogenesis" to ---angiogenesis---.

Column 2, line 56, change "ANN.N.Y." to ---A.N.Y.---.

Column 2, line 62, change "ACAD." to ---Acad.---.

Column 3, line 58, change "antigiostatic" to ---angiostatic---.

Column 4, line 52, change "immunemediated" to ---immune-mediated---.

Column 7, line 9, change "alial" to ---alia---.

Column 8, line 57, change "DMS" to ---DMSO---.

Column 10, line 24, change "effect" to ---effective---.

Column 10, line 44, change "$S_3Y$" to ---$SO_3Y$---.

UNITED STATES PATENT AND TRADEMARK OFFICE
CERTIFICATE OF CORRECTION

PATENT NO. : 4,820,693
DATED : April 11, 1989
INVENTOR(S) : L. Gillespie

It is certified that error appears in the above-identified patent and that said Letters Patent is hereby corrected as shown below:

Column 12, line 12, change "as to --a--.

Column 14, line 24, change "as to --a--.

Signed and Sealed this

Twenty-third Day of October, 1990

Attest:

HARRY F. MANBECK, JR.

*Attesting Officer*　　*Commissioner of Patents and Trademarks*